US00PP31389P2

(12) United States Plant Patent
O'Connell

(10) Patent No.: US PP31,389 P2
(45) Date of Patent: Jan. 21, 2020

(54) ***ECHINOPSIS HYBRIDA CRISTATA* 'MYSTIC MAZE'**

(50) Latin Name: *Echinopsis hybrida*
Varietal Denomination: Mystic Maze

(71) Applicant: Altman Specialty Plants, Inc, Vista, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,545

(22) Filed: Nov. 30, 2018

(51) Int. Cl.
*A01H 5/12* (2018.01)
*A01H 6/24* (2018.01)

(52) U.S. Cl.
USPC ..... Plt./372

(58) Field of Classification Search
USPC ..... Plt./373, 263.1, 372
See application file for complete search history.

(56) References Cited

U.S. PATENT DOCUMENTS

PP28,946 P2 * 2/2018 O'Connell ..... A01H 5/02
Plt./372

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Echinopsis* cultivar named 'Mystic Maze' is disclosed, characterized by a unique *cristata* plant form. magenta and orange flowers in a triple whorl produced over a 6 to 7-month period. Plants are fast growing and robust, resulting in both improved propagation rates and improved finished plant production times. *Echinopsis* is an ornamental cactus, useful as an indoor ornamental plant and outdoors in warm climates.

3 Drawing Sheets

Latin name of the genus and species: *Echinopsis hybrida cristata.*

Variety denomination: 'MYSTIC MAZE'.

BACKGROUND OF THE INVENTION

The new cultivar, *Echinopsis* 'Mystic Maze', was found by the inventor, Renee O'Connell, as the result of a naturally occurring whole plant mutation. The parent variety is the patented proprietary variety referred to as *Echinopsis* 'Flambeau' U.S. Plant Pat. No. 28,946. Selection of the new variety was made April of 2013.

Asexual reproduction of the new cultivar 'Mystic Maze' was first performed in Vista, Calif., during the Summer of 2013 at a commercial greenhouse, by vegetative cuttings. 'Mystic Maze' has since produced multiple generations and has shown that the unique features of this cultivar are stable and reproduced true to type.

SUMMARY OF THE INVENTION

The cultivar 'Mystic Maze' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Mystic Maze'. These characteristics in combination distinguish 'Mystic Maze' as a new and distinct *Echinopsis* cultivar:

1. Unique *cristata* form. The new variety is a cristate mutation of *Echinopsis* 'Flambeau', a patented plant, registered as U.S. Plant Pat. No. 28,946. Cristation is not common among *Echinopsis* (*Chamaelobivia*) hybrids; in fact, the only other known cristate is the type species *Echinopsis chamaecereus* (*Chamaecereus silvestrii*) cristatus.
2. *Echinopsis cristata* 'Mystic Maze' forms whorls of cristate growth, rarely or never producing a non cristate shoot.
3. *Echinopsis cristata* 'Mystic Maze' is robust growing, producing a large crest in less than a year from a 9 cm pot, enhancing the production time in a commercial environment.
4. As *Echinopsis cristata* 'Mystic Maze' is fast growing, and whorls are produced quickly, it is possible to propagate many cuttings from a larger plant, thereby enhancing propagation time in a commercial nursery environment.

PARENTAL COMPARISON

Plants of the new cultivar 'Mystic Maze' are similar to plants of the seed parent, in most horticultural characteristics, however, plants of the new cultivar 'Mystic Maze' differ in the following;

1. *Echinopsis cristata* 'Mystic Maze' varies from *Echinopsis* 'Flambeau' U.S. Plant Pat. No. 28,946 in that the growth is produced in cristate or fasciate whorls, rather than stem offsets (peanuts) from a central plant stem.
2. *Echinopsis cristata* 'Mystic Maze' has not been observed to flower, whereas *Echinopsis* 'Flambeau' U.S. Plant Pat. No. 28,946 is very floriferous.
3. *Echinopsis cristata* 'Mystic Maze' does not have an upright morphology as does *Echinopsis* 'Flambeau' U.S. Plant Pat. No. 28,946, due to the morphology of the cristation, the growth is more spherical and lateral.

COMMERCIAL COMPARISON

Plants of the new cultivar 'Mystic Maze' are comparable to the unpatented, commercial variety *Echinopsis chamae-*

*cereus* cristatus. The two *Echinopsis* varieties are similar in most horticultural characteristics; however, the new variety 'Mystic Maze' differs in the following:

1 *Echinopsis cristata* 'Mystic Maze' grows larger and can fill a gallon pot in less than a year, whereas *Echinopsis chamaecereus* cristatus is a smaller growing plant.
2. *Echinopsis cristata* 'Mystic Maze' rarely forms non-cristate stems, whereas *Echinopsis chamaecereus* cristatus forms non-cristate stems more frequently.
3. *Echinopsis chamaecereus* cristatus produces flowers on the "normal" shoots, a characteristic not observed of *Echinopsis cristata* 'Mystic Maze' as it rarely produces "normal" (flowering) shoots.

Plants of the new cultivar 'Mystic Maze' can also be comparable to the unpatented commercial variety *Echinopsis multiplex* cristatus. The two *Echinopsis* varieties are similar in most horticultural characteristics; however, the new variety 'Mystic Maze' differs in the following:

1. *Echinopsis cristata* 'Mystic Maze' grows much faster than *Echinopsis oxygona* cristatus, enhancing production times in a commercial nursery environment.
2. *Echinopsis cristata* 'Mystic Maze' produces cristate growth with many more whorls than *Echinopsis oxygona* cristatus, which tends to produce thicker, but less numerous whorls of growth.
3. In a commercial nursery environment, the propagation of new crests of *Echinopsis cristata* 'Mystic Maze', due to the more robust growth and significantly more numerous production of cristate whorls, is more enhanced than that of *Echinopsis oxygona* cristatus.
4. *Echinopsis oxygona* cristatus does occasionally produce lilac tinted white flowers on the cristate growth, whereas *Echinopsis cristata* 'Mystic Maze' has not been observed to flower on the cristate growth.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Echinopsis hybrida cristata* 'Mystic Maze'. Photographs provided by the breeder.

DETAILED BOTANICAL DESCRIPTION

Figure 1:
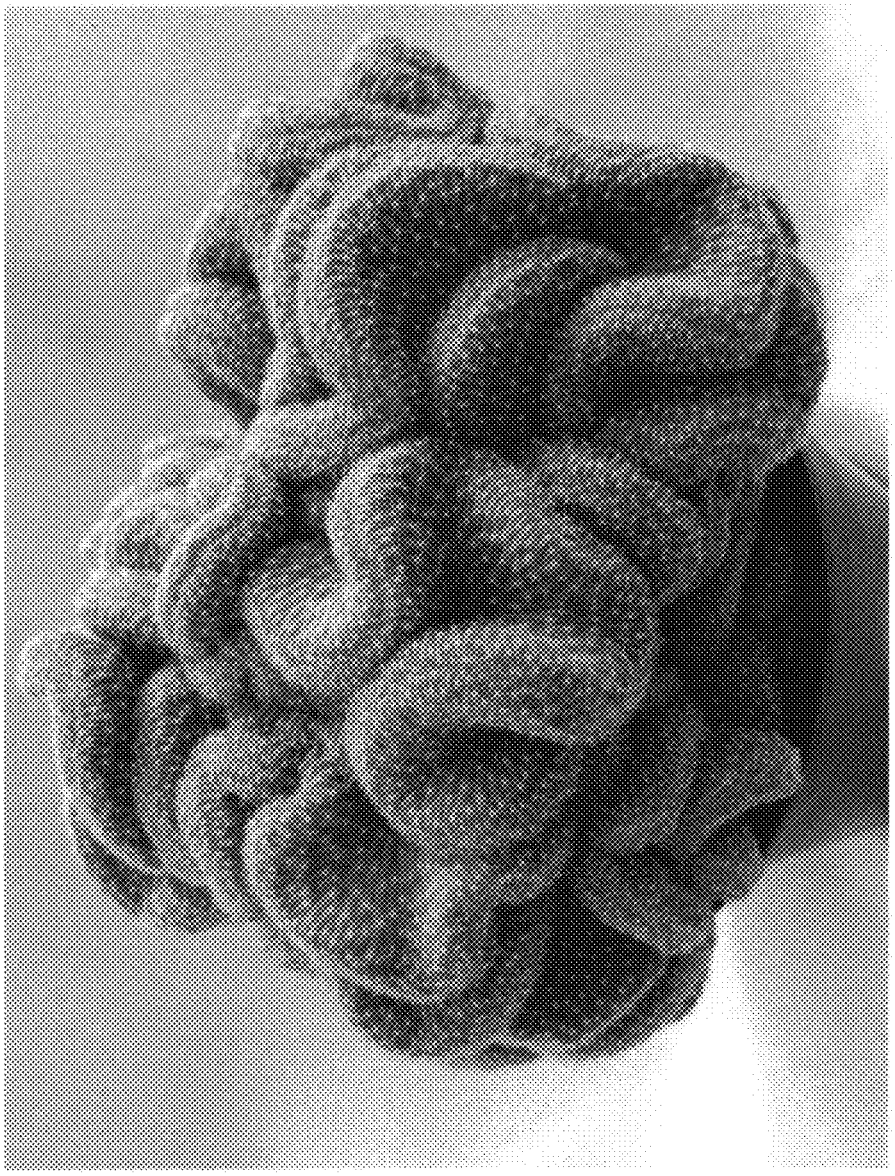
FIG. 1 illustrates in full color *Echinopsis hybrida cristata* 'Mystic Maze', grown in a greenhouse (approximately 3000-foot candles) in Vista, Calif. The plant is in a 1-gallon pot and photographed at an angle showing a side view of the plant.
Figure 2:
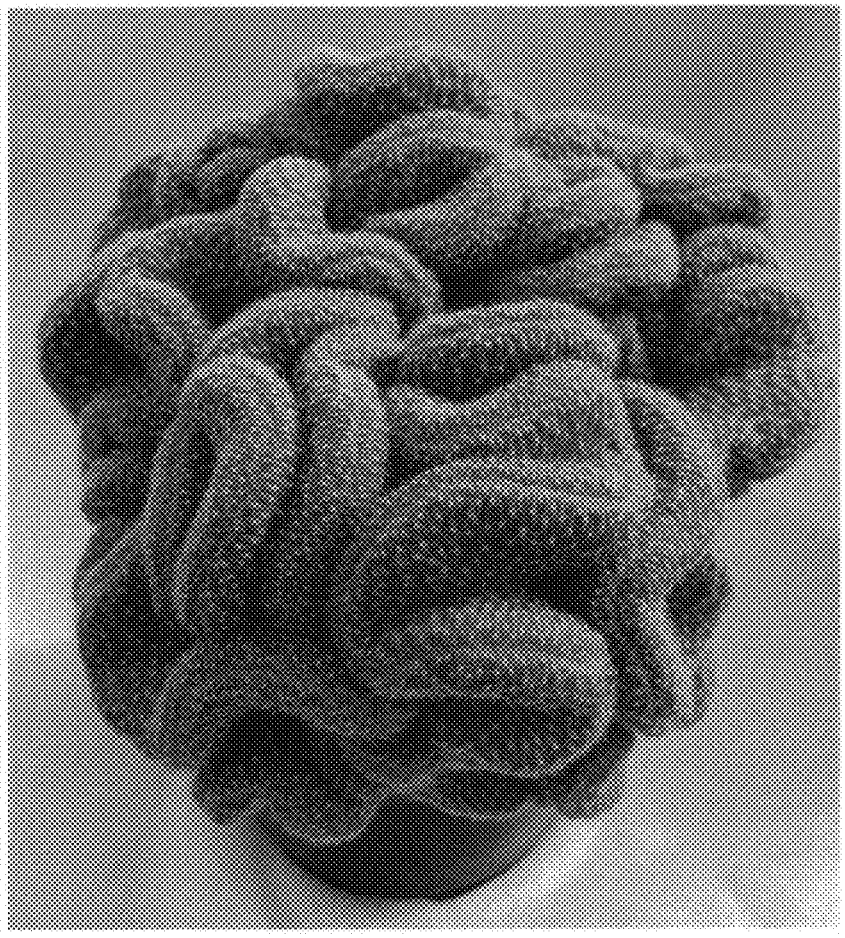
FIG. 2 illustrates in full color a top view angle of the same plant of *Echinopsis hybrida cristata* 'Mystic Maze', grown in a greenhouse (approximately 3000-foot candles) in Vista, Calif.
Figure 3:
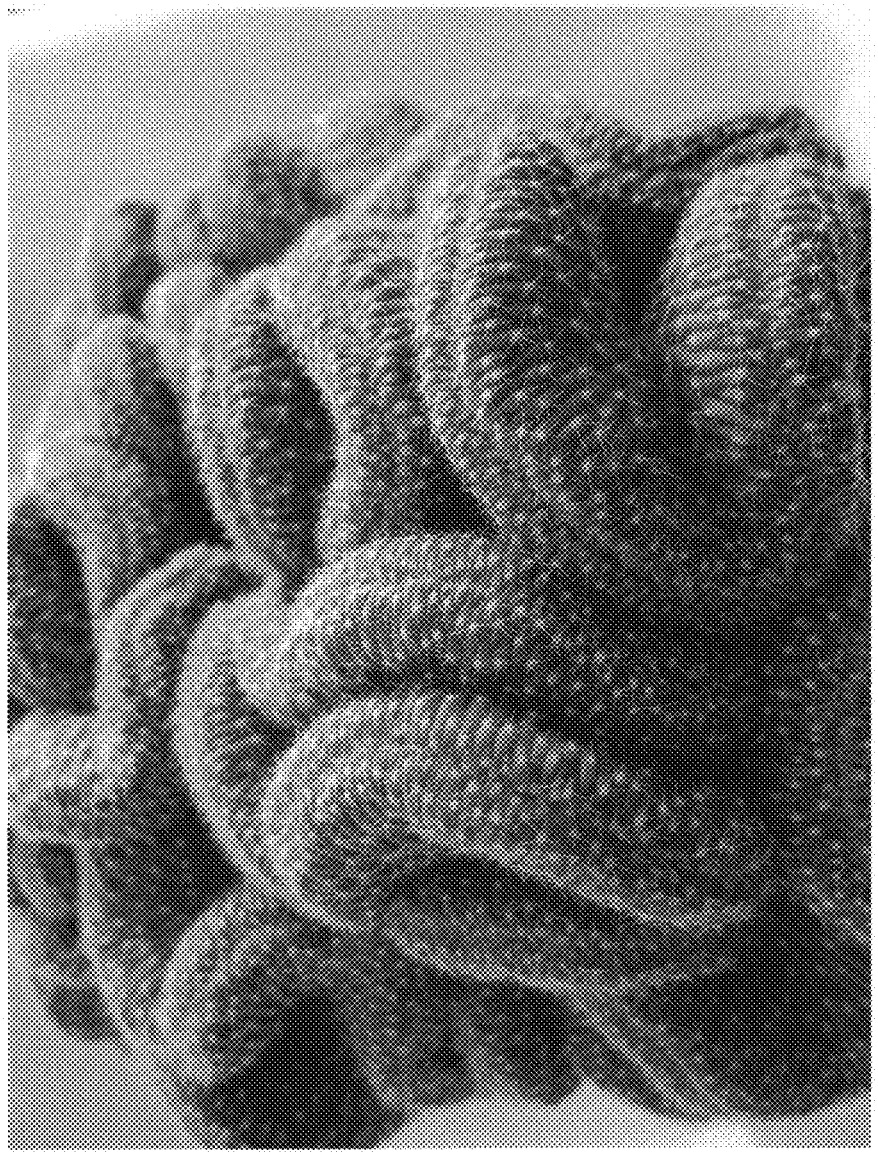
FIG. 3 illustrates in full color a closeup of *Echinopsis hybrida cristata* 'Mystic Maze', grown in a greenhouse (approximately 3000-foot candles) in Vista, Calif.

In the following description, color references are made to The Royal Horticultural Society Colour Chart, 2007, except where general terms of ordinary dictionary significance are used. The following observations and measurements describe *Echinopsis hybrida cristata* 'Mystic Maze' plants in a commercial shade house in Vista, Calif. Temperatures ranged from 34° F. to 90° F. night and day. No artificial light, photoperiodic treatments or chemical treatments were given to the plants. Natural light conditions were approximately 2500-4000-foot candles of light. Measurements and numerical values represent averages of typical plant types.

Botanical classification: *Echinopsis hybrida cristata* 'Mystic Maze'.

PROPAGATION

Type of propagation typically used: Vegetative cuttings.

Root description: Brown to tan, fibrous, non-woody, non-fleshy. Moderately dense.

PLANT

General plant description: Round, mounded cactus composed of tightly compact and swirled crests.

Growth habit: Mounded.

Plant spread: Approximately 18.0 to 21.0 cm, in a 1-gallon pot.

Plant height: Approximately 10 to 12 cm.

Growth rate: Rapid.

Stem description: No stem.

Crests: Crests tightly compressed together and swirled.

Quantity of crest swirls: About 50 on a 1-gallon pot, of approximately 14 months old from a rooted cutting.

Size: Crests about 13 to 15 mm in width. Depth varies, typically 5 mm to 30 mm.

Color: Near Green 138A. Sometimes lightly flushed Greyed-Red 178A.

Ridges: 2 to 3 mm wide. Length 5 to 30 mm, same as depth of crest. Height about 2 mm.

Areole:

*Spacing.*—Approximately 2 to 4 mm apart on top of crest. Less dense on sides of crest, near 9 to 12 mm.

*Size.*—1 to 2 mm.

*Color.*—Near RHS Yellow-White 158D, composed of dense trichomes less than 1 mm long.

Spine/thorn description:

*Arrangement.*—Spines radially arranged. No central spine.

*Quantity.*—Typically 7 to 9.

*Length.*—2.0 to 2.5 mm.

*Color.*—Near White 155A.

Age of plant described: Approximately 14 months from a rooted cutting.

FLOWER

Not observed to date.

OTHER CHARACTERISTICS

Temperature tolerance: USDA zones 10 and above.

Disease/pest resistance: Neither resistance nor susceptibility to typical pathogens or pests of *Echinopsis* has been observed.

Drought tolerance: Extreme tolerance for drought.

What is claimed is:

1. A new and distinct cultivar of *Echinopsis hybrida cristata* form plant named 'Mystic Maze' as herein illustrated and described.

* * * * *